US006797152B2

(12) United States Patent
Freund et al.

(10) Patent No.: US 6,797,152 B2
(45) Date of Patent: Sep. 28, 2004

(54) SENSORS AND SENSING METHODS FOR DETECTING ANALYTES BASED ON CHANGES IN PKA OF A SENSING POLYMER

(75) Inventors: Michael S. Freund, Sierra Madre, CA (US); Eiichi Shoji, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 340 days.

(21) Appl. No.: 09/919,657

(22) Filed: Jul. 31, 2001

(65) Prior Publication Data

US 2002/0029979 A1 Mar. 14, 2002

Related U.S. Application Data

(60) Provisional application No. 60/222,276, filed on Jul. 31, 2000, provisional application No. 60/258,486, filed on Dec. 27, 2000, and provisional application No. 60/261,334, filed on Jan. 12, 2001.

(51) Int. Cl.[7] .................. G01N 27/26; G01N 27/04; G01N 21/75

(52) U.S. Cl. .............. 205/792; 204/403.01; 422/82.02; 422/82.05

(58) Field of Search ...................... 204/403.01, 415, 204/416, 433; 205/777.5, 778, 789, 792; 422/82.05, 82.02

(56) References Cited

PUBLICATIONS

Taj, S., et al., "Relationship between permselectivity and the acidity of polyphenols pertaining to the pH response of Pt/polyphenol electrode," *Synthethic Metals* 97, pp. 205–209, 1998.

Pringsheim, E., et al., "Optical sensing of pH using thin films of substituted polyanilines," *Analytica Chimica Acta* 357, pp. 247–252, 1997.

Boyer, M.–I., et al., "Vibrational Analysis of Polyaniline: A Model Compound Approach," *J. Phys. Chem. B*, vol. 102, No. 38, pp. 7382–7392, 1998.

Kikuchi, A., et al., "Glucose–Sensing Electrode Coated with Polymer Complex Gel Containing Phenylboronic Acid," *Analytical Chemistry*, vol. 68, No. 5, pp. 823–828, Mar. 1, 1996.

Moore, A.N.J., et al., "Redox switching of carbohydrate binding to ferrocene boronic acid," *Can. J. Chem.*, vol. 77, pp. 681–686, 1999.

(List continued on next page.)

*Primary Examiner*—Kaj K. Olsen
(74) *Attorney, Agent, or Firm*—Fish & Richardson P.C.

(57) ABSTRACT

Sensor systems and sensing methods for detecting one or more analytes in a fluid. A sensor includes a polymer capable of undergoing a proton-coupled redox reaction. The polymer includes a plurality of reactive substituents capable of undergoing a reaction with an analyte. Upon exposure of the sensor to a fluid containing the analyte, a response is detected based on a change in the $pK_a$ of the polymer.

64 Claims, 3 Drawing Sheets

PUBLICATIONS

Hatchett, D.W., et al., "Acid Doping of Polyaniline: Spectroscopic and Electrochemical Studies," *J. Phys. Chem. B*, vol. 103, No. 50, pp. 10992–10998, 1999.

McQuade, D.T., et al., "Conjugated Polymer–Based Chemical Sensors," *Chem. Rev.*, vol. 100, No. 7, pp. 2537–2574, 2000.

Nicolas, M., et al., "New Boronic–Acid– and Boronate–Substituted Aromatic Compounds as Precursors of Fluoride–Responsive Conjugated Polymer Films," *Eur. J. Org. Chem.*, pp. 1703–1710, 2000.

Karyakin, A.A., et al., "Processible polyaniline as an advanced potentiometric pH transducer. Application to biosensors," *Analytical Chemistry*, vol. 71, No. 13, pp. 2534–2540, Jul. 1, 1999.

Sotzing, G.A., et al., "Highly Sensitive Detection and Discrimination of Biogenic Amines Utilizing Arrays of Polyaniline/Carbon Black Composite Vapor Detector," *Chem. Mater.*, vol. 12, No. 3, pp. 593–595, 2000.

James, T.D., et al., "Saccharide Sensing with Molecular Receptors Based on Boronic Acid," *Angew. Chem. Int. Ed. Engl.*, vol. 35, pp. 1910–1922, 1996.

Shoji, E., et al., "Potentiometric Sensors Based on the Inductive Effect on the $pK_a$ of Poly(aniline): A Nonenzymatic Glucose Sensor," *J. Am. Chem. Soc.*, vol. 123, No. 14, pp. 3383–3384, 2001 (published on Web Mar. 16, 2001).

Bartlett, P.N., et al., "Poly(aniline)–poly(acrylate) composite films as modified electrodes for the oxidation of NADH," *Phys. Chem. Phys.*, vol. 2, pp. 2599–2606, 2000.

Barker, S.A., et al., "The Interaction of Areneboronic Acids with Monosaccharides," *Carbohydrate Research*, vol. 26, pp. 33–40, 1973.

Bartlett, P.N., et al., "Electroactivity, stability and application in an enzyme switch at pH of 7 poly(aniline)–poly(styrensulfonate) composite films," *J. Chem. Soc., Faraday Tans.*, vol. 92, pp. 4137–4143, 1996.

SENSORS AND SENSING METHODS FOR DETECTING ANALYTES BASED ON CHANGES IN PKA OF A SENSING POLYMER

CROSS REFERENCE TO RELATED APPLICATIONS

This application claims the benefit under 35 U.S.C. §119 (e) of Provisional Applications Nos. 60/222,276, filed Jul. 31, 2000, 60/258,486, filed Dec. 27, 2000, and 60/261,334, filed Jan. 12, 2001, and 60/308,723 filed on Jul. 30, 2001, each of which is incorporated by reference herein.

TECHNICAL FIELD

This invention relates to sensor systems for detecting analytes in fluids.

BACKGROUND

The development of chemical sensors has been the focus of intense research since the 1960s. Recently, conjugated polymers have received considerable attention for use in sensor applications, both as electronic conductors and as active sensing elements with ligands coupled to the polymer backbone. Poly(aniline), in particular, has received attention due to its proton coupled redox chemistry and its resulting pH dependant properties. For example, poly(aniline) has been used as a pH electrode and has been coupled to reactions that generate or consume protons to create sensors.

SUMMARY

In general, in one aspect, the invention features methods for detecting analytes in a fluid. According to the methods, a sensor is provided that includes a polymer capable of undergoing a proton-coupled redox reaction, which polymer includes a plurality of reactive substituents capable of undergoing a reaction with an analyte. The sensor is exposed to a fluid containing the analyte, and a response is detected based on a change in the $pK_a$ of the polymer.

In general, in another aspect, the invention features non-enzymatic sensor systems for detecting an analyte in a fluid. The systems include a fluid volume, a sensor in operable contact with the fluid volume, and a detector configured to detect a response when the sensor is exposed to a fluid in the fluid volume. The sensor includes a substrate having a surface, and a sensor film deposited on the substrate surface. The sensor film includes a polymer capable of undergoing a proton-coupled redox reaction. The polymer includes a plurality of reactive substituents capable of undergoing a reaction with an analyte. The response is detected based on a change in the $pK_a$ of the polymer.

Particular embodiments can include one or more of the following features. The plurality of reactive substituents can include two or more chemically different reactive substituents. The two or more chemically different reactive substituents can have selectivity for different analytes and/or different effects on the $pK_a$ of the polymer. One or more of the reactive substituents can have an inductive effect and/or a resonance effect on the $pK_a$ of the polymer. The analyte can react with one or more of the reactive substituents upon exposure of the sensor film to the fluid to cause a change in the $pK_a$ of the polymer.

The sensor can include one or more conjugated polymers. At least one of the conjugated polymers can be selected from the group consisting of polyaniline, poly(o-phenylenediamine), poly(o-aminophenol), polyphenoxazine, polyphenothiazine, and poly(aminonaphtalene). The polymer can be a functionalized polyaniline, such as a poly(aniline boronic acid) (e.g., a homopolymer of 3-aminophenylboronic acid).

At least a plurality of the reactive substituents can be selected from the group consisting of boronic acids, pyridines, bipyridines and thiols. The analyte can be selected from the group consisting of polyols, fluorides, and amines. The analyte can be a metal selected from the group of metals capable of forming a complex with a ligand selected from the group consisting of pyridines, bipyridines and thiols. One or more of the reactive substituents can be capable of undergoing a reversible or irreversible reaction with the analyte. The polymer can be a poly(aniline boronic acid), and the analyte a polyol.

The response can be a change in the electrochemical potential of the sensor relative to a reference electrode, or a change in pH, conductivity, impedance, color, or mass of the sensor.

The analyte can be identified based on the detected response. Where one or more of the reactive substituents is capable of reacting with a plurality of different analytes, the analyte can be identified by distinguishing between at least one analyte in the fluid and at least one of the plurality of different analytes capable of reacting with the reactive substituents based on the detected response. Similarly, where one or more of the reactive substituents is capable of reacting with a plurality of different analytes, the analyte can be identified by distinguishing between a plurality of different analytes in the fluid based on the detected response. The concentration of the analyte in the fluid, or a change in that concentration, can be identified based on the detected response. If the sensor is exposed to the fluid for a time sufficient to allow the reaction between the reactive substituents and the analyte to reach an equilibrium, the response can be measured at the equilibrium.

The details of one or more embodiments of the invention are set forth in the accompanying drawings and the description below. Other features, objects, and advantages of the invention will be apparent from the description and drawings, and from the claims.

DESCRIPTION OF DRAWINGS

Like reference symbols in the various drawings indicate like elements.

DETAILED DESCRIPTION

Figure 1:
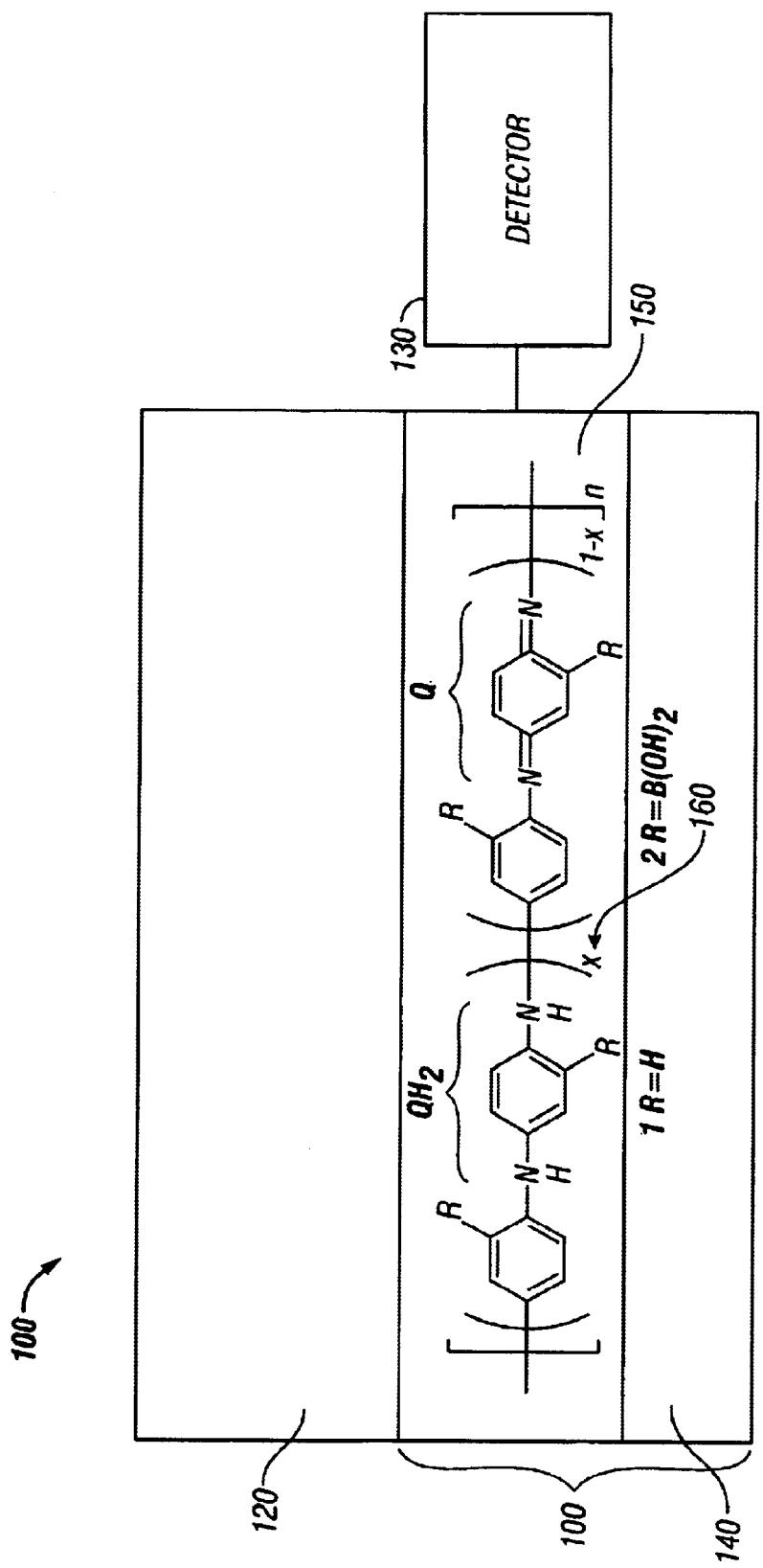
FIG. 1 illustrates one embodiment of a sensor system for detecting an analyte in a fluid.

FIG. 1 illustrates one implementation of a sensor system 100 for detecting an analyte or analytes in a fluid (which, as used in this specification, includes liquid and gaseous solutions containing an amount of the analyte, as well as substantially pure liquid or gaseous samples of the analyte alone). System 100 includes a sensor 110 situated in operable contact with a sampling volume 120 and a detector 130 operably coupled to sensor 110. Sensor 110 includes a sensor substrate 140, such as a conventional glassy carbon electrode or the like, and a sensor film 150 deposited on a surface of the sensor substrate. Sensor film 150 is formed from a functionalized polymer 160 that is capable of undergoing a proton-coupled redox reaction. Polymer 160 is functionalized with a plurality of reactive substituents, which can be chemically identical (e.g., as in a homopolymer derived from a plurality of monomers bearing an identical or different substituents) or chemically different (e.g., as in a copolymer derived from monomers bearing different substituents), such that the introduction of a fluid containing a target analyte or analytes into sampling volume 120 results in a measurable response based on a change in the $pK_a$ of the polymer. Optionally, sensor 110 can include multiple sensors of similar or diverse construction, as in a sensor array.

Polymer 160 can be any polymer that is capable of undergoing a proton-coupled redox reaction, and is functionalized with one or more reactive substituents that are capable of undergoing a selective reaction with one or more target analytes. Those skilled in the art will recognize that the selection of a particular reactive substituent or substituents is based on the particular analyte or class of analytes in question. Thus, for example, boronic acids are known to undergo selective, reversible complexation with polyols (e.g., compounds containing more than one hydroxy group, such as glucose and other saccharides), fluorides and amines. Accordingly, boronic acid substituents can be selected where sensor selectivity for these compounds is desired. Some examples of other potentially useful substituents include pyridines, bipyridines, and thiols, which are known to selectively form complexes with metals such as iron, iridium, and gold.

In other embodiments, the reactive substituents may undergo irreversible reactions with the target analyte or analytes. For example, boronic acid substituents may undergo facile ipso-substitution reactions under mild conditions with a variety of compounds such as halogens, nitrates, thiols and the like, as described in the co-pending provisional application Serial No. 60/308,723, filed on Jul. 30, 2001 and naming Ejichi Shoji and Michael S. Freund as inventors, which is incorporated by reference herein, resulting in replacement of the boronic acid substituent with a substituent derived from the analyte. Such irreversible reactions can form the basis of sensor systems for detecting the presence of target analytes, as will be described in more detail below.

In a preferred embodiment, discussed below, polymer 160 is a conjugated polymer such as a functionalized polyaniline. However, those skilled in the art will recognize that other polymers are capable of undergoing proton-coupled redox reactions, and are therefore suitable for use in the sensors and sensing methods described herein. Some other examples of such polymers include poly(o-phenylenediamine), poly(o-aminophenol), polyphenoxazine, polyphenothiazine, poly (aminonaphtalene).

Without wanting to be bound by theory, preferably the reactive substituents exert an effect (e.g., an inductive or resonance effect) on the $pK_a$ of the polymer, which effect changes upon reaction of the substituent with the target analyte or analytes, thereby changing the polymer's $pK_a$. Thus, upon exposure of the sensor film to a target analyte, the analyte reacts with the reactive substituent. The resulting change in the properties of the reactive substituent causes a change in the polymer's $pK_a$, which can be detected by a variety of known techniques.

Detector 130 is configured to receive and process response signals based on changes in the $pK_a$ of polymer 160. In various implementations, detector 130 can be configured to receive and process such signals based on a variety of conventional measurements reflecting changes in sensor $pK_a$, which can include, for example, changes in electrochemical potential, conductivity, or impedance of the sensor polymer. In addition, changes in $pK_a$ can be associated with changes in the polymer's color or mass resulting from reaction of the analyte with the reactive substituents.

Optionally, detector can include appropriate signal-processing electronics and/or a programmable processor for processing the response signals. In some embodiments, detector 130 is coupled to a computer system 170, such as a general purpose computer system of conventional construction, that may include a programmable processor running a signal processing program for identifying analytes and/or characteristics thereof based on the response signals received from sensor 110.

Figure 2:
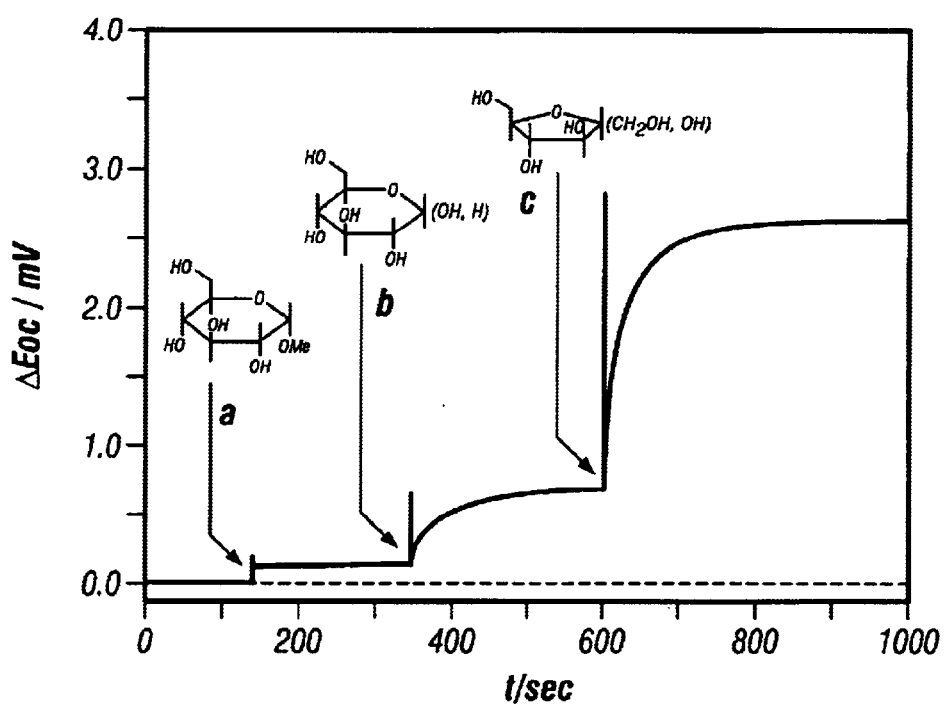
FIG. 2 is a response curve of a poly(aniline boronic acid) electrode as a function of time upon addition of 6.8 mM: a) α-Methyl-D-glucoside; b) D-glucose; and c) fructose in pH 7.4 PBS.

A method 200 of using sensor system 100 to detect the presence of an analyte is illustrated in FIG. 2. A fluid is introduced into sampling volume 120 (step 210). If the analyte is present in the fluid, reactive substituents associated with the sensor film interact with the analyte (step 220), thereby causing a change in the $pK_a$ of the polymer. Detector 130 detects and records response signals from sensor 110 (step 230). Optionally, detector 130 (or a processor of computer 170) processes the response signals further to detect and/or characterize an analyte or combination of analytes (step 240). The results of this detection and processing can be reported to a user, or can prompt computer 170 to initiate other appropriate action.

Sensor systems 100 can be fabricated using known techniques. Techniques for preparing conducting polymers are well known (e.g., electrochemical polymerization), and can be used to prepare functionalized conducting polymers as films or layers on suitable sensor substrates (e.g., on the surface of a glassy carbon electrode), such as is described in the provisional application entitled "Poly(aniline boronic acid): A New Precursor to Substituted Poly(aniline)s", filed Jul. 30, 2001, which was incorporated by reference above. Optionally, stabilizing agents can be incorporated in the polymer film—for example, the immobilization of polyanions such as polystyrene sulfonate or Nafion during polymerization of polyaniline is known to increase the redox stability of polyaniline films, as reported by P. N. Bartlett et al., *J. Chem. Soc. Faraday Trans.* 1996, 92, 4137–4143.

Sensors 110 can be incorporated into a sensing system 100 by electrically coupling sensor 110 to an electrical measuring device in detector 130. The device measures changes in signal at sensor 110, preferably as the signal varies over time. The signal can be, for example, open circuit potential, conductivity, impedance or some other physical property of the sensor material capable of changing in response to the presence of the analyte in the fluid. The device can include signal processing electronics, and can be used in conjunction with a computer and data structures for identifying an unknown analyte or analytes by, for example, comparing a given response or response profile to a structure-response database for qualitative and quantitative analysis.

In one mode of operation, sensor 110 incorporates one or more sensor polymers that respond differently to changes in analyte concentration or identity. Thus, detector 130 detects and records a first response when sensor 110 is exposed to a first fluid containing an amount of a first analyte, and a second response when sensor 110 is exposed to a second analyte or to a second amount of the first analyte.

In some implementations, sensor 110 will be constructed so that the reaction between the reactive substituents is a reversible reaction (e.g., complexation of boronic acids with polyols as described above), such that sensor 110 is capable of continuously monitoring for the presence or concentration of an analyte or analytes in a fluid, or for changes in composition of an analyte mixture. Alternatively, sensor 110 can be constructed as a single use sensor, useful, for example, simply to detect whether the sensor has been exposed to an analyte, in which case the reactive substituents may undergo irreversible reaction with the target analyte or analytes. Thus, for example, a poly(aniline boronic acid) sensor can be used to detect the presence of a molecular halogen in a solution simply by locating the sensor in a headspace above the solution. Exposure of the sensor to halogen vapor from the solution can lead to an ipso-substitution reaction replacing the sensor's boronic acid substituent(s) with halogen groups as described above, which may, in turn result in a change in the substituent's inductive effect on the $pK_a$ of the polymer (i.e., where the inductive properties of the new substituent differ from those of the original boronic acid substituent). The resulting change in the polymer $pK_a$ can be detected by monitoring, e.g., the conductivity of the polymer, as discussed above.

Thus, for example, one embodiment of a sensor system 100 provides a non-enzymatic glucose sensor based on the reversible complexation reaction between boronic acid and diols, illustrated in Scheme 1, below.

Scheme 1

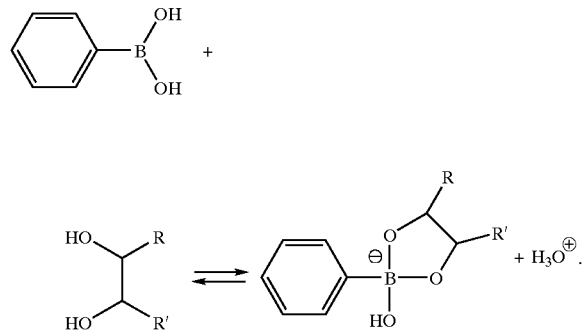

Poly(aniline) 1 consists of benzenoid diamine and quinone diimine groups, where the distribution of these groups is a function of the oxidation state of the polymer, and the degree of protonation of the polymer is a function of the pH.

Since the redox chemistry of 1 involves both electrons and protons, the open circuit voltage, $E_{oc}$, is sensitive to changes in pH. Likewise, it can be shown that the $E_{oc}$ will be a function of $K_a$. For example, the acid-base reaction associated with the quinone diimine group in 1 can be written as:

$$Q + 2H^+ \rightleftharpoons QH_2^{2+} \tag{1}$$

with the corresponding acid dissociation constant:

$$K_a = [Q][H^+]^2/[QH_2^{2+}] \tag{2}$$

The reduction of the protonated quinone diimine structure is given by:

$$QH_2^{2+} + 2e^- \rightleftharpoons QH_2 \tag{3}$$

with the corresponding Nernst expression:

$$E = E^{o'}{}_{QH_2^{2+}/QH_2} + (RT/2F)ln[QH_2^{2+}]/[QH_2] \tag{4}$$

It follows that the net proton coupled redox reaction, (combining eqs 1 and 3) is:

$$Q + 2H^+ + 2e^- \rightleftharpoons QH_2 \tag{5}$$

Substituting the expression for $[QH_2^{2+}]$ obtained from eq 2 into eq 4 yields the corresponding Nernst expression for the net reaction, which is a function of $K_a$:

$$E = E^{o'}{}_{QH_2^{2+}/QH_2} + (RT/2F)ln[Q][H^+]^2/K_a[QH_2] \tag{6}$$

It then follows that stabilizing $QH_2^{2+}$ by increasing the electron donating ability of a substituent group, in this case converting boronic acid into the boronate anion complex (Scheme 1, above), will reduce the $K_a$ of the protonated quinone diimine group (increasing $E_{oc}$, see eq 6).

A sensor incorporating a poly(aniline boronic acid) film was prepared by the electrochemical polymerization of 3-aminophenylboronic acid on a glassy carbon electrode in the presence of Nafion as described in the following Examples, which are intended to illustrate the methods and apparatus described above, and not to otherwise limit the scope of the claims that follow below.

EXAMPLES

Reagents.

3-aminophenylboronic acid (ABA), Nafion (40 wt % alcohol-water mixed solution), sodium fluoride, D-glucose (GL), fructose (FR), and α-methyl-D-glucoside were purchased from Aldrich and used as purchased. Phosphate buffer saline (PBS) stock solution, pH 7.4, (x10 concentrated stock) was purchased from EM Science. The water that was used for all experiments was purified and deionized (18.3 mega ohm) by pure water system (Branstead, Model: Easy pure RF).

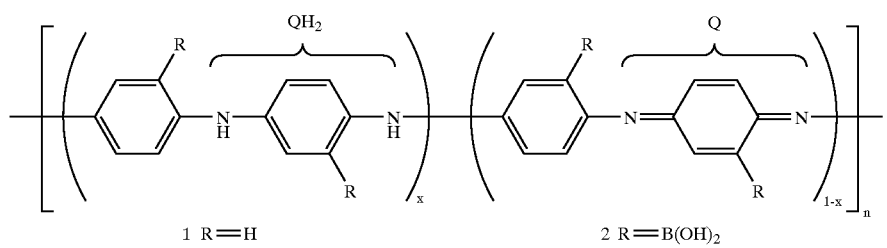

1 R═H    2 R═B(OH)$_2$

Instrumental Setup.

Glassy carbon electrodes (3 mm diameter) were purchased from Bioanalytical Science. The open circuit potential measurements were performed on an electrochemical workstation system (CH Instruments, model 660) connecting PC computer (Dell Optiplex GX-1). Cyclic voltammetry was performed with a potentiostat (EG&G Model: 362). In the voltammetric experiments, a three-electrode configuration was used including a platinum wire (length: 50 cm, diameter: 0.2 mm) counter electrode and a saturated calomel electrode (SCE) as reference. XPS spectra were recorded with an M-Probe surface spectrometer (Surface Science Instruments). All spectra were recorded with focused and monochromatized Al $K\alpha_{1,2}$ irradiation (hv=1486.6 eV), and the X-ray beam was incident on the surface at an angle of 55° with respect to the surface normal. The analyzer was also positioned at an angle of 55° with respect to the surface normal.

Open Circuit Measurements.

25 mL of phosphate buffer saline (PBS, commercially available stock solution as 137 mM NaCl, 2.7 mM KCl, 10 mM phosphate buffer, pH 7.4) was placed in an electrochemical cell. A PABA electrode, equilibrated in PBS was placed in the cell and an open circuit measurement was made versus an SCE. The solution in the cell was stirred continuously during the measurements. Analyte was injected from a concentrated stock solution. For example, for glucose, 612.5 mg of D-glucose was dissolved in 4 mL PBS and the resulting solution was used as concentrated stock solution allowing 3.4 mM changes in concentration per 100 µL injection. Measurements were made under ambient conditions (ca.25° C.) with no strict control over temperature.

Deposition of Poly(Aniline Boronic Acid).

The oxidative polymerization of 3-aminophenylboronic acid was performed producing poly(aniline-3-boronic acid) (PABA) as follows: 3-aminophenylboronic acid (40 mM) and sodium fluoride (40 mM) were dissolved in 25 mL sulfuric acid aqueous solution (0.5 M) containing 5 mM Nafion (commercially available 40 wt % Nafion alcohol-water mixture solution was used). The potential of the GC electrode was scanned between 0.0 and 1.1 V vs. SCE at a scan rate of 100 mV/s. Polymerization was halted when the charge passed for the reduction of the deposited polymer reached 0.34 mC. The production of the PABA layer had a deep greenish blue color similar to that obtained upon the formation of poly(aniline). X-ray photoelectron spectra of 2 showed that after equilibrating in PBS, all fluoride was exchanged out of the film. After careful washing of the layer with pure water, the electrode was stored in pH 7.4 PBS buffer to settle its chemical potential Measurement of Open Circuit Potentials for Different Diols.

The state of the polymer was followed by monitoring $E_{oc}$ versus SCE in PBS as the sensor was exposed to solutions containing varying concentrations of α-methyl-D-glucoside, glucose and fructose, as illustrated in FIG. 2. The difference in sensitivity of the sensor for these three analytes is shown by the change in $E_{oc}$ upon the addition of the same concentrations of the different sugars, and qualitatively follows the difference in binding constants with phenylboronic acid reported in neutral aqueous solutions (fructose>glucose>α-methyl-D-glucoside).

Due to the sensitivity of 1 to pH, it is expected that the $E_{oc}$ will be sensitive to the local pH drop within the film associated with the formation of the complex (Scheme 1). This was confirmed by observing increases in $E_{oc}$ for 1 coated with poly(vinylphenylboronic acid) upon the addition of glucose. However, as expected, the responses associated with local pH changes were transient in nature due to the rapid return to equilibrium with the bulk solution. Similar transient increases in $E_{oc}$ are observed as spikes in FIG. 2 upon the addition of different sugars.

The slower steady-state responses that are observed in FIG. 2 are consistent with a change in $pK_a$ of 1 and subsequent protonation. It should be noted that the positive change in $E_{oc}$ is in contrast to the change in redox behavior expected for the inductive effect on an isolated redox center that does not involve the transfer of protons. For example, according to the results obtained with the boronic acid substituted ferrocene/ferrocenium redox couple, reported by A. Moore et al., Can. J. Chem. 1999, 77, 681–686, the apparent formal potential decreases upon formation of the electron donating boronate anion structure.

Measurement of Open Circuit Potentials for Changing Glucose Concentration.

Figure 3A:
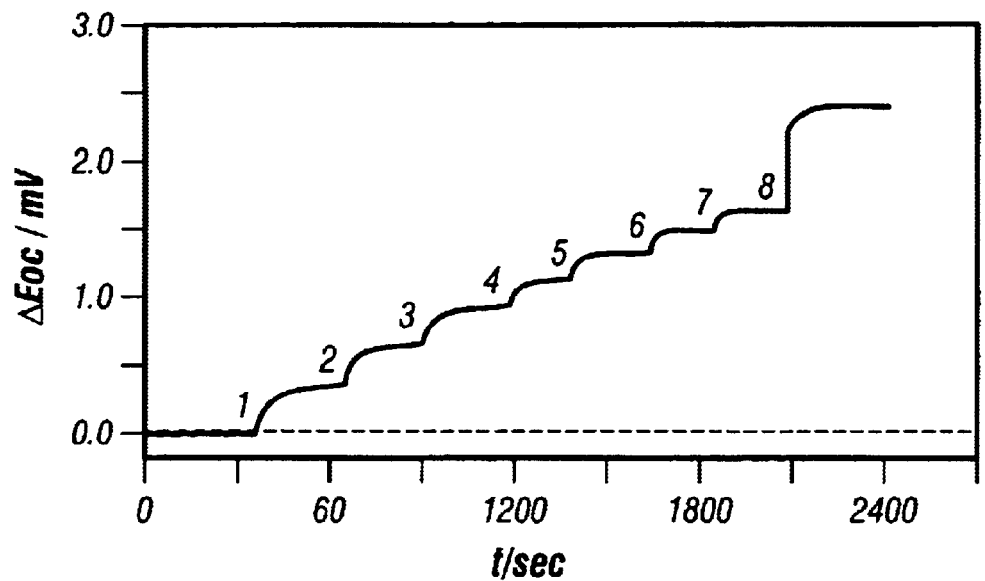
FIG. 3a is a D-Glucose response curve of a poly(aniline boronic acid) electrode in pH 7.4 PBS as a function of time. Additions resulted in the following series of concentrations: 1) 3.4; 2) 6.8; 3) 10.2; 4) 13.6; 5) 17.0; 6) 20.4; 7) 23.8; and 8) 40.8 mM.
Figure 3B:
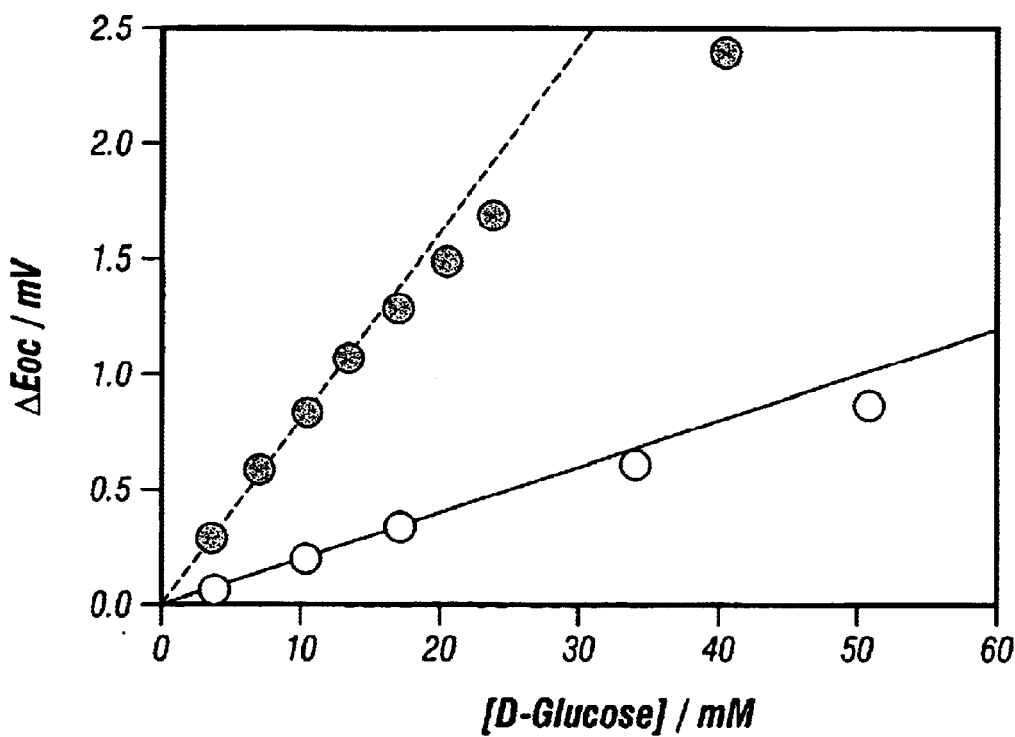
FIG. 3b illustrates calibration curves of D-glucose (filled circles) for a poly(aniline boronic acid) electrode and of D-glucose (open circles) for poly(aniline) coated electrode in pH 7.4 PBS.

FIG. 3 illustrates the use of a poly(aniline boronic acid) sensor to detect varying concentrations of glucose, including a response profile for the exposure of the sensor to eight different glucose concentrations at pH 7.4, as well as calibration curves of glucose for the poly(aniline boronic acid) sensor film and a polyaniline control. As FIG. 3 shows, the addition of glucose results in a stepwise increase in $E_{oc}$. A control experiment using only polyaniline 1 exhibited similar increases in $E_{oc}$, but the total shift of the potential was clearly smaller. Reversibility of the sensor was confirmed by the return of the $E_{oc}$ to its initial value upon exposure to blank PBS.

A number of embodiments of the invention have been described. Nevertheless, it will be understood that various modifications may be made without departing from the spirit and scope of the invention. For example, while the sensors and sensing methods have been described in the context of particular polymers, reactive substituents and analytes, it will be apparent to those skilled in the art that the sensors and sensing methods can be implemented using other reactive substituents as well, and in particular that any of a variety of known ligand/substrate systems may be suitable for use in the sensors and sensing methods described herein. Likewise, while the sensor polymers illustrated herein are typically substantially homopolymers having one or more reactive substituents coupled to each monomer, those skilled in the art will recognize that the sensors and sensing methods can be implemented using functionalized copolymers having different reactive substituents coupled to different monomers, or, in some implementations, using less than one reactive substituent per monomer so long as the sensor response upon exposure to the relevant analyte levels is sufficiently high for the chosen detection technique. Accordingly, other embodiments are within the scope of the following claims.

What is claimed is:

1. A method for detecting one or more analytes in a fluid, comprising:

providing a sensor including a polymer capable of undergoing a proton-coupled redox reaction, the polymer comprising two or more chemically different reactive substituents capable of undergoing a reaction with an analyte;

exposing the sensor to a fluid containing the analyte; and detecting a response to the exposure of the sensor to the analyte based on a change in the $pK_a$ of the polymer.

2. The method of claim 1, wherein:

the two or more chemically different reactive substituents have selectivity for different analytes.

3. The method of claim 1, wherein:

the two or more chemically different reactive substituents have different effects on the $pK_a$ of the polymer.

4. The method of claim 1, wherein:

the reactive substituents have an inductive effect on the $pK_a$ of the polymer.

5. The method of claim 1, wherein:

the reactive substituents have a resonance effect on the $pK_a$ of the polymer.

6. The method of claim 1, wherein:

the analyte reacts with the reactive substituents upon exposure of the sensor film to the fluid to cause a change in the $pK_a$ of the polymer.

7. The method of claim 1, wherein:

the sensor includes one or more conjugated polymers.

8. The method of claim 7, wherein:

at least one of the conjugated polymers is selected from the group consisting of polyaniline, poly(o-phenylenediamine), poly (o-aminophenol), polyphenoxazine, polyphenothiazine, and poly (aminonaphtalene).

9. The method of claim 1, wherein:

the polymer is a functionalized polyaniline.

10. The method of claim 1, wherein:

the polymer is a poly(aniline boronic acid).

11. The method of claim 10, wherein:

the poly(aniline boronic acid) is substantially a homopolymer of 3-aminophenylboronic acid.

12. The method of claim 1, wherein:

at least a plurality of the reactive substituents are selected from the group consisting of boronic acids, pyridines, bipyridines and thiols.

13. The method of claim 1, wherein:

the analyte is selected from the group consisting of polyols, fluorides, and amines.

14. The method of claim 1, wherein:

the analyte is a metal selected from the group of metals capable of forming a complex with a ligand selected from the group consisting of pyridines, bipyridines and thiols.

15. The method of claim 1, wherein:

the reactive substituents are capable of undergoing a reversible reaction with the analyte.

16. The method of claim 15, wherein:

the sensor is exposed to the fluid for a time sufficient to allow the reaction between the reactive substituents and the analyte to reach an equilibrium; and detecting the response includes measuring the response at the equilibrium.

17. The method of claim 1, wherein:

the reactive substituents are capable of undergoing an irreversible reaction with the analyte.

18. The method of claim 1, wherein:

the polymer is a poly(aniline boronic acid); and the analyte is a polyol.

19. The method of claim 1, wherein:

the response is a change in the electrochemical potential of the sensor relative to a reference electrode.

20. The method of claim 1, wherein:

the response is a change in pH.

21. The method of claim 1, wherein:

the response is a change in the conductivity of the sensor.

22. The method of claim 1, wherein:

the response is a change in the impedance of the sensor.

23. The method of claim 1, wherein:

the sensor has a color; and the response is a change in the color of the sensor.

24. The method of claim 1, wherein:

the sensor has a mass; and the response is a change in the mass of the sensor.

25. The method of claim 1, further comprising:

identifying the analyte based on the detected response.

26. The method of claim 25, wherein:

the reactive substituents are capable of reacting with a plurality of different analytes; and identifying the analyte includes distinguishing between at least one analyte in the fluid and at least one of the plurality of different analytes capable of reacting with the reactive substituents based on the detected response.

27. The method of claim 25, wherein:

the reactive substituents are capable of reacting with a plurality of different analytes; and identifying the analyte includes distinguishing between a plurality of different analytes in the fluid based on the detected response.

28. The method of claim 25, further comprising:

identifying a concentration of the analyte in the fluid based on the detected response.

29. The method of claim 28, further comprising:

exposing the sensor to a second fluid;

detecting a second response; and identifying a change in the concentration of the analyte based on the response and the second response.

30. A sensor system for detecting an analyte in a fluid, comprising:

a fluid volume;

a sensor located in operable contact with the fluid volume, the sensor including a substrate having a surface, and a sensor film deposited on the substrate surface, the sensor film including a polymer capable of undergoing a proton-coupled redox reaction, the polymer comprising two or more chemically different reactive substituents capable of undergoing a reaction with an analyte; and a detector configured to detect a response based on a change in the $pK_a$ of the polymer when the sensor is exposed to a fluid in the fluid volume.

31. The sensor system of claim 30, wherein:

the two or more chemically different reactive substituents have selectivity for different analytes.

32. The sensor system of claim 30, wherein:

the two or more chemically different reactive substituents have different effects on the $pK_a$ of the polymer.

33. The sensor system of claim 30, wherein:

the reactive substituents have an inductive effect on the $pK_a$ of the polymer.

34. The sensor system of claim 30, wherein:

the reactive substituents have a resonance effect on the $pK_a$ of the polymer.

35. The sensor system of claim 30, wherein:

the analyte reacts with of the reactive substituents upon exposure of the sensor film to the fluid to cause a change in the $pK_a$ of the polymer.

36. The sensor system of claim 30, wherein:
the sensor film includes one or more conjugated polymers.

37. The sensor system of claim 36, wherein:
at least one of the conjugated polymers is selected from the group consisting of polyaniline, poly(o-phenylenediamine), poly(o-aminophenol), polyphenoxazine, polyphenothiazine, and poly(aminonaphtalene).

38. The sensor system of claim 30, wherein:
the polymer is a functionalized polyaniline.

39. The sensor system of claim 30, wherein:
the polymer is a poly(aniline boronic acid).

40. The sensor system of claim 39, wherein:
the poly(aniline boronic acid) is substantially a homopolyrner of 3-aminophenylboronic acid.

41. The sensor system of claim 30, wherein:
one or more of the polymers are prepared by a process including the electrochemical polymerization of 3-aminophenylboronic acid.

42. The sensor system of claim 30, wherein:
the reactive substituents are selected from the group consisting of boronic acids, pyridines, bipyridines and thiols.

43. The sensor system of claim 30, wherein:
the analyte is selected from the group consisting of hydroxides, fluorides, and amines.

44. The sensor system of claim 30, wherein:
the analyte is a metal selected from the group of metals capable of forming a complex with a ligand selected from the group consisting of pyridines, bipyridines and thiols.

45. The sensor system of claim 30, wherein:
the reactive substituents are capable of undergoing a reversible reaction with the analyte.

46. The sensor system of claim 30, wherein:
the reactive substituents are capable of undergoing an irreversible reaction with the analyte.

47. The sensor system of claim 30, wherein:
the polymer is a poly(aniline boronic acid); and
the analyte is a polyol.

48. The sensor system of claim 30, wherein:
the response is a change in the electrochemical potential of the sensor film relative to a reference electrode.

49. The sensor system of claim 30, wherein:
the response is a change in pH.

50. The sensor system of claim 30, wherein:
the response is a change in the conductivity of the sensor film.

51. The sensor system of claim 30, wherein:
the response is a change in the impedance of the sensor film.

52. The sensor system of claim 30, wherein:
the sensor film has a color; and
the response is a change in the color of the sensor film.

53. The sensor system of claim 30, wherein:
the sensor film has a mass; and
the response is a change in the mass of the sensor film.

54. The sensor system of claim 30, further comprising:
a programmable processor coupled to the detector, the processor being configured to identify the analyte based on the detected response.

55. The sensor system of claim 54, wherein:
the reactive substituents are capable of reacting with a plurality of different analytes; and
the programmable processor is operable to distinguish between at least one analyte in the fluid and at least one of the plurality of different analytes capable of reacting with the reactive substituents based on the detected response.

56. The sensor system of claim 54, wherein:
the reactive substituents are capable of reacting with a plurality of different analytes; and
the programmable process is operable to distinguish between a plurality of different analytes in the fluid based on the detected response.

57. The sensor system of claim 54, wherein:
the programmable processor is operable to identify a concentration of the analyte in the fluid based on the detected response.

58. The sensor system of claim 57, wherein:
the detector is configured to detect a second response when the sensor film is exposed to a second fluid; and
the programmable processor is operable to identify a change in the concentration of the analyte based on the response and the second response.

59. The sensor system of claim 30, wherein:
the detector is configured to measure the response at an equilibrium of the reaction between the reactive substituents and the analyte.

60. A sensor system for detecting an analyte in a fluid, comprising:
means providing a sensor film including a polymer capable of undergoing a proton-coupled redox reaction, the polymer comprising two or more chemically different reactive substituents capable of undergoing a reaction with an analyte;
means for exposing the sensor film to a fluid containing the analyte; and
means for detecting a response to the exposure of the sensor film to the analyte based on a change in the $pK_a$ of the polymer.

61. A method for detecting one or more analytes in a fluid, comprising:
providing a sensor comprising a poly(aniline boronic acid) polymer capable of undergoing a proton-coupled redox reaction, the polymer including a plurality of reactive substituents capable of undergoing a reaction with an analyte;
exposing the sensor to a fluid containing the analyte; and
detecting a response to the exposure of the sensor to the analyte based on a change in the pKa of the polymer.

62. A sensor system for detecting an analyte in a fluid, comprising:
a fluid volume;
a sensor located in operable contact with the fluid volume, the sensor including a substrate having a surface, and a sensor film deposited on the substrate surface, the sensor film comprising a poly(aniline boronic acid) polymer capable of undergoing a proton-coupled redox reaction, the polymer including a plurality of reactive substituents capable of undergoing a reaction with an analyte; and
a detector configured to detect a response based on a change in the pKa of the polymer when the sensor is exposed to a fluid in the fluid volume.

63. A method for detecting one or more analytes in a fluid, comprising:
providing a sensor comprising a polymer capable of undergoing a proton-coupled redox reaction, the polymer including a plurality of reactive substituents capable of undergoing a reaction with an analyte;

exposing the sensor to a fluid containing the analyte; and detecting a response to the exposure of the sensor to the analyte based on a change in the pKa of the polymer, wherein the response is selected from the group consisting of a change in electrochemical potential, a change in conductivity, a change in impedance, a change in mass, and any combination of the foregoing.

64. A sensor system for detecting an analyte in a fluid, comprising:

a fluid volume;

a sensor located in operable contact with the fluid volume, the sensor including a substrate having a surface, and a sensor film deposited on the substrate surface, the sensor film comprising a polymer capable of undergoing a proton-coupled redox reaction, the polymer including a plurality of reactive substituents capable of undergoing a reaction with an analyte; and a detector configured to detect a response based on a change in the pKa of the polymer when the sensor is exposed to a fluid in the fluid volume, wherein the response is selected from the group consisting of a change in electrochemical potential, a change in conductivity, a change in impedance, a change in mass, and any combination of the foregoing.

* * * * *